United States Patent [19]
Brion et al.

[11] Patent Number: 5,622,957
[45] Date of Patent: Apr. 22, 1997

[54] BENZOPYRROLIZINOQUINOLIZINONES

[75] Inventors: Jean-Daniel Brion, Saint-Leu-la-Foret; Claude Thal, Sceaux; Luc Demuynck, Orleans; Jean-Gilles Parmentier, Issy les Moulineaux; Jean Lepagnol, Chaudon; Pierre Lestage, Paris; Jean-François Pujol, Lyons; Pascal Schmitt, Metz-Queleu; Pierre Potier, Paris, all of France

[73] Assignee: Adir et Compagnie, Courbevoie, France

[21] Appl. No.: 433,163

[22] Filed: May 3, 1995

Related U.S. Application Data

[62] Division of Ser. No. 354,660, Dec. 13, 1994, Pat. No. 5,602,131.

[30]  Foreign Application Priority Data

Dec. 14, 1993  [FR]  France ................. 93 14944

[51] Int. Cl.$^6$ .............................................. A61K 31/475
[52] U.S. Cl. .................... 514/279; 514/280; 546/36; 546/41; 546/51; 546/70
[58] Field of Search ........................ 546/42, 43, 51, 546/36, 41; 514/280, 279

[56]  References Cited

U.S. PATENT DOCUMENTS

| | | | |
|---|---|---|---|
| 3,755,335 | 8/1973 | Thal et al. ........................... | 546/51 |
| 4,283,401 | 8/1981 | Szantay et al. ...................... | 546/51 |
| 4,366,157 | 12/1982 | Ono et al. ........................... | 546/51 |
| 4,464,535 | 8/1984 | Szantay et al. ...................... | 546/51 |
| 4,716,162 | 12/1987 | Tomita et al. ....................... | 546/42 |
| 5,034,396 | 7/1991 | Aktogo ............................... | 546/51 |

OTHER PUBLICATIONS

Sarlet et al, Chemical Abstr. vol. 91, entry 74767f (1979).

*Primary Examiner*—Donald G. Daus
*Attorney, Agent, or Firm*—The Firm of Gordon W. Hueschen

[57]  ABSTRACT

A compound selected from those of general formula (I):

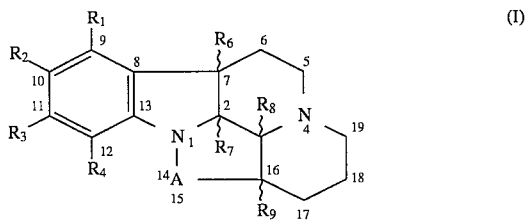

(I)

wherein A represents a bivalent radical

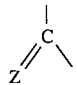

and $R_1$, $R_2$, $R_3$, $R_4$, $R_6$, $R_7$, $R_8$, $R_9$ and Z are as defined in the description, the isomers and pharmaceutically-acceptable acid or base addition salts thereof, and medicinal products containing the same which are useful in the treatment of depression and anxiety.

4 Claims, No Drawings

BENZOPYRROLIZINOQUINOLIZINONES

The present application is a division of our prior-filed copending application Ser. No. 08/354,660, filed Dec. 13, 1994, now U.S. Pat. No. 5,602,131.

This present invention relates to new eburnane analogues, to a process for the preparation thereof and to pharmaceutical compositions containing them.

The literature provides numerous examples of compounds exhibiting an eburnane structure. This is the case especially of U.S. Pat. No. 3,454,583 which deals with vincamine (methyl (3α, 14β,16α)-14,15-dihydro-14-hydroxy-eburnamenine-14-carboxylate) and its derivatives for their vasodilatory properties. Applications FR-A-2 433 528 and FR-A-2 381 048 present new 20,21-dinoreburnamenine compounds and application EP-A-287 468 presents new 17-aza-20,21-dinoreburnamenine compounds.

The compounds of the present invention are distinguished from those of the prior art by modifications made to the ring containing the 14 and 15 atoms of the eburnane skeleton.

Apart from their novel structure, the Applicants have discovered that the compounds of the invention exhibit very valuable pharmacological properties. In particular, they have been found to be powerful selective or non-selective inducers of tyrosine hydroxylase.

The present invention relates more especially to the compounds of the general formula (I):

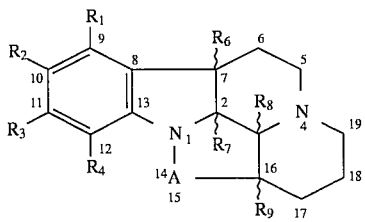

wherein:

$R_1$, $R_2$, $R_3$ and $R_4$, which may be identical or different, are:

selected independently of one another from:

a hydrogen atom, a halogen atom, a hydroxy radical, a linear or branched ($C_1$–$C_6$)-alkyl radical optionally substituted by one or more halogen atoms, by one or more amino groups, by one or more nitro groups, by one or more linear or branched ($C_1$–$C_6$)-alkoxy groups and/or by one or more aryl radicals, selected from phenyl and naphthyl, which are themselves optionally substituted by one or more halogen atoms, nitro, amino groups, ($C_1$–$C_6$)-alkyl and/or ($C_1$–$C_6$)-alkoxy radicals, and a linear or branched ($C_1$–$C_6$)-alkoxy group optionally substituted by one or more halogen atoms, by one or more amino groups, by one or more nitro groups, and/or by one or more linear or branched ($C_1$–$C_6$)-alkoxy groups, or $R_1$, $R_2$, $R_3$ and $R_4$, taken in pairs and carried by adjacent carbon atoms, form a methylenedioxy or ethylenedioxy group, $R_6$ and $R_7$: either each simultaneously represent hydrogen, adopting a cis-configuration with respect to one another, or together form a bond, $R_8$ and $R_9$: either each simultaneously represent hydrogen, adopting a cis- or trans-configuration with respect to one another, or together form a bond, in the case $R_6$ and $R_7$ also together form a bond,

represents a bivalent radical selected from

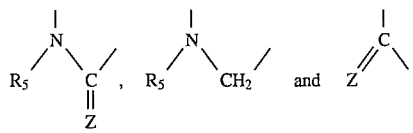

Z is selected from oxygen and sulfur, $R_5$ is selected from hydrogen and a linear or branched ($C_1$–$C_6$)-alkyl group optionally substituted by one or more:

halogen atoms, linear or branched ($C_1$–$C_6$)-alkoxy radicals, phenyl radicals, optionally being substituted by one or more linear or branched ($C_1$–$C_6$)-alkyl radicals, and/or linear or branched ($C_1$–$C_6$)-alkoxy radicals, those alkyl and alkoxy radicals optionally being substituted by one or more aryl radicals, selected from phenyl and naphthyl, which are unsubstituted or substituted by one or more groups selected from the halogens, amino, nitro, ($C_1$–$C_6$)-alkyl and/or ($C_1$–$C_6$)-alkoxy radicals.

and/or radicals

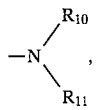

wherein $R_{10}$ and $R_{11}$ are selected independently of one another from hydrogen, linear or branched ($C_1$–$C_6$)-alkyl radicals and linear or branched ($C_1$–$C_6$)-alkoxy radicals, their possible N-oxides, enantiomers and diastereoisomers and also, where appropriate, their pharmaceutically acceptable acid addition salts.

Of the acids that can be used to form the pharmaceutically acceptable salts of the compounds of the invention, there may be mentioned by way of non-limiting example hydrochloric, hydrobromic, sulfuric and phosphoric acid and acetic, propionic, maleic, fumaric, tartaric, nitric, oxalic, benzoic, methanesulfonic, isethionic and benzenesulfonic acid.

The invention extends also to a process for the preparation of the compounds of formula (I), characterised in that the compound of formula (II) (the method of synthesis of which is described by R. N. Schut and T. J. Leipzig, *J. Het. Chem.*, 3, (1966), 101–102):

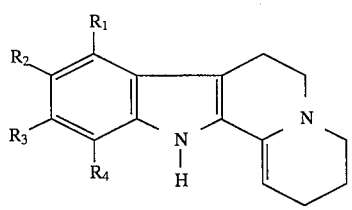

wherein $R_1$, $R_2$, $R_3$ and $R_4$ are as defined in formula (I), is subjected to the action of a compound of formula (III):

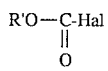

(III)

wherein R' represents an alkyl group containing from 1 to 6 carbon atoms in a straight or branched chain, and Hal represents a halogen atom,
to yield the compound of formula (IV):

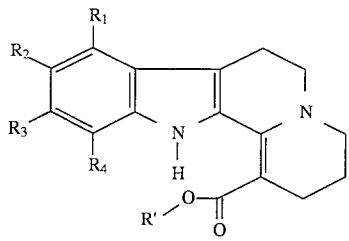

(IV)

wherein $R_1$, $R_2$, $R_3$, $R_4$ and R' are as defined above, which is then hydrogenated to form a mixture of cis-enantiomers of formula (Va):

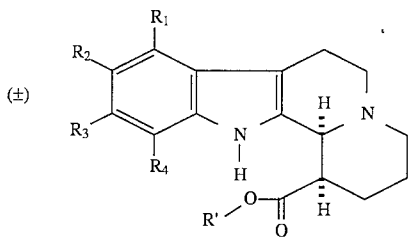

(Va)

wherein $R_1$, $R_2$, $R_3$, $R_4$ and R' are as defined above, by the action of a hydrogenation agent, such as sodium cyanoborohydride, in an acid medium, for example acetic acid, and in an anhydrous solvent, such as tetrahydrofuran, it optionally being possible for an epimerisation reaction to be effected, at a low temperature, for example at 0° C., in an anhydrous solvent, such as dimethoxyethane, using an alkali metal hydride, such as sodium hydride, in order to obtain a mixture of trans-enantiomers of formula (Vb):

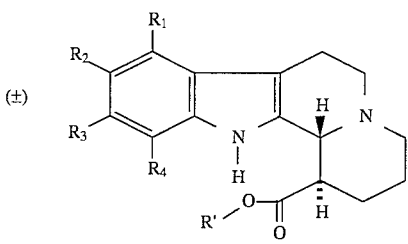

(Vb)

wherein $R_1$, $R_2$, $R_3$, $R_4$ and R' are as defined above, the totality of the compounds of formulae (Va) and (Vb) forming the totality of the compounds of formula (V):

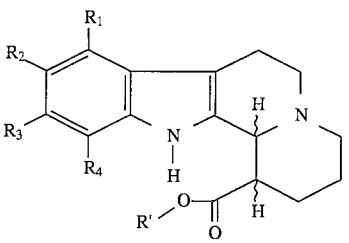

(V)

wherein $R_1$, $R_2$, $R_3$, $R_4$ and R' are as defined above, which compounds of formula (V) are again subjected to hydrogenation, in a trifluoroacetic acid medium, by means of sodium cyanoborohydride, to yield the compound of formula (VI):

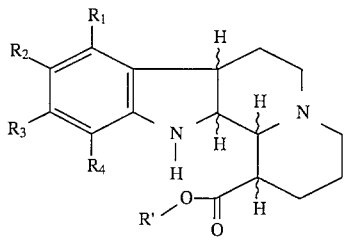

(VI)

wherein $R_1$, $R_2$, $R_3$, $R_4$ and R' are as defined above, which is subjected:

either: A/ to the action of an alkali metal hydride, for example sodium hydride, in an anhydrous solvent, such as tetrahydrofuran, under reflux, to yield the compound of formula (Xa):

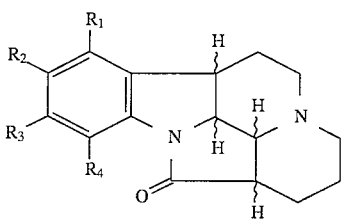

(Xa)

wherein $R_1$, $R_2$, $R_3$ and R4 are as defined above, or: B/ to the action of sodium nitrite, in an acid medium, for example acetic acid, then in the presence of zinc, to yield the hydrazine of formula (VII):

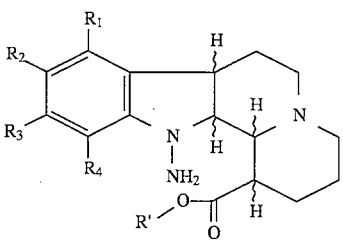

(VII)

wherein $R_1$, $R_2$, $R_3$, $R_4$ and R' are as defined above, which is then cyclised, under the action of an alkali metal hydride, for example sodium hydride, to form a compound of formula (VIII):

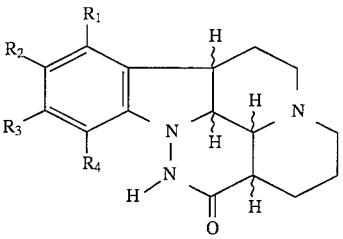

(VIII)

wherein $R_1$, $R_2$, $R_3$ and $R_4$ are as defined above.
and then subjected, if desired, to the action of the compound of formula (IX):

(IX)

wherein $R'_5$ has the same meanings as the radical $R_5$, with the exception of hydrogen, and Hal represents a halogen atom, after the action of a deprotonating agent, for example n-butyllithium or sodium hydride, to yield the compound of formula (Xb):

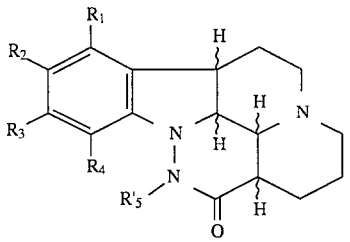

wherein $R_1$, $R_2$, $R_3$, $R_4$ and $R'_5$ are as defined above, it being possible, if desired, for the ketone function of the totality of the compounds of formulae (VIII), (Xa) and (Xb) to be reduced, for example by lithium aluminium hydride, to form the corresponding hydrocarbon, or subjected to the action of Lawesson's reagent, in order to be converted into the corresponding thioketone, the totality of the compounds of formulae (VIII), (Xa) and (Xb), as well as their possible reduction products or their possible thio analogues, forming the totality of the compounds of formula (I/1):

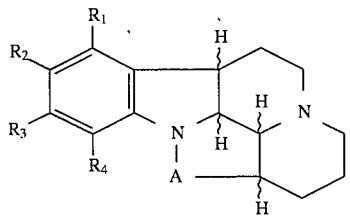

wherein $R_1$, $R_2$, $R_3$, $R_4$ and A are as defined above, which are:

either: subjected to the action of a gentle oxidising agent, such as manganese dioxide, to yield the compound of formula (I/2):

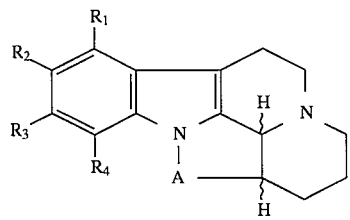

wherein $R_1$, $R_2$, $R_3$, $R_4$ and A are as defined above, or: subjected to the action of a strong oxidising agent, such as nitric acid in acetic acid, to yield the compound of formula (I/3):

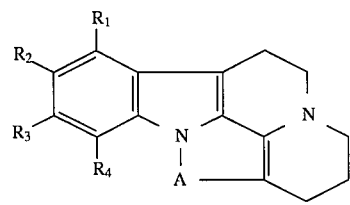

wherein $R_1$, $R_2$, $R_3$, $R_4$ and A are as defined above, the totality of the compounds of formulae (I1), (I2) and (I3) forming the totality of the compounds of formula (I) which are, where appropriate, purified by a conventional purification technique, separated into their possible enantiomers and diastereoisomers, for example by chromatography on a column of the Chiralpak AD type, and/or converted into their N-oxides or pharmaceutically acceptable acid addition salts.

The compound of formula (V) can also be prepared starting from the compound of formula (XI):

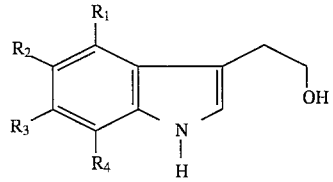

wherein $R_1$, $R_2$, $R_3$ and $R_4$ are as defined above, which is converted into a compound of formula (XII):

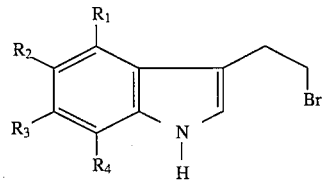

wherein $R_1$, $R_2$, $R_3$ and $R_4$ are as defined above, by the action of a bromination agent, such as carbon tetrabromide in the presence of triphenylphosphine, or phosphorus tribromide, which is then reacted with a compound of formula (XIII):

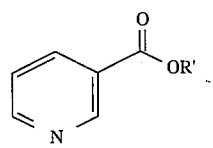

wherein R' is as defined above.

to yield, after catalytic hydrogenation, then cyclisation in an acid medium, the compound of formula (V) as defined above.

The compounds of formula (I) possess valuable pharmacological properties, especially that of being powerful inducers of tyrosine hydroxylase (TH). It is known that tyrosine hydroxylase is a limiting enzyme which controls, in particular, the synthesis of the transmitter in the central catecholaminergic and dopaminergic neurones. The speed of synthesis of that transmitter is, especially, linked with the appearance of tonic dysfunctions of the brain, which is what numerous human behavioural pathologies, such as anxiety, psychoses, depression, etc. are.

Owing to their capacity to induce tyrosine hydroxylase, the compounds of the invention can be used therapeutically in the treatment of depression, anxiety, memory disorders in the course of senescence and/or degenerative diseases, and in the treatment of Parkinson's disease.

The present invention relates also to pharmaceutical compositions that contain as active ingredient at least one compound of the general formula (I), one of its N-oxides or one of its pharmaceutically acceptable acid addition salts, alone or in combination with one or more suitable inert, non-toxic excipients or carriers.

The pharmaceutical compositions so obtained are generally presented in dosage form. They may, for example, be in the form of tablets, dragées, gelatin capsules, suppositories or injectable or drinkable solutions and may be administered orally, rectally, intramuscularly or parenterally.

The dosage may vary especially in accordance with the age and weight of the patient, the mode of administration, the nature of the disorder, and associated treatments, and consists of closes of from 0.1 to 100 mg taken from one to five times per day.

The following Examples illustrate the invention, but without limiting it in any way. The starting materials are known or are prepared on the basis of known procedures.

Preparation A: Ethyl trans-9-chloro-1,2,3,4,6,7,12,12b-octahydro-indolo[2,3-a]quinolizine-1-carboxylate Stage A: Ethyl 9-chloro-2,3,4,6,7,12-hexahydro-indolo[2,3-a]quinolizine-1-carboxylate 18 g of 9-chloro-2,3,4,6,7,12-hexahydroindolo[2,3-a]quinolizine, obtained in accordance with the process described in Patent FR-A-2 315 277, are dissolved in 500 cm³ of toluene and 16.5 cm³ of diisopropylethylamine. The whole is heated to 80° C. and then 11.4 g of ethyl chloroformate are added over a period of 15 minutes. The reaction medium is then maintained at 80° C. for 10 hours and then, after returning to ambient temperature, is chromatographed on a silica gel column (eluant: dichloromethane) and yields the expected product.

Yield: 36%

Melting point: 82°–83° C.

Stage B: Ethyl cis-9-chloro-1,2,3,4,6,7,12,12b-octahydro-indolo[2,3-a]quinolizine-1-carboxylate 8.0 g of the compound obtained in the previous stage are dissolved in 200 cm³ of anhydrous tetrahydrofuran and 8 cm³ of acetic acid.

The whole is cooled to approximately from 0° C. to 5° C. using an ice-bath. 1.7 g of sodium cyanoborohydride are then added under argon over a period of 15 minutes. After stirring for 20 minutes at ambient temperature, the reaction medium is hydrolysed by adding 25 cm³ of a 5% aqueous sodium carbonate solution. The tetrahydrofuran is distilled off in vacuo and the reaction medium is taken up in 100 cm³ of dichloromethane and 100 cm³ of water. After customary, treatment of the organic phase, the oily residue obtained is chromatographed on a silica gel column (eluant: dichloromethane/methanol, 95:5) to yield the expected product.

Yield: 90%

Stage C: Ethyl trans-9-chloro-1,2,3,4,6,7,12,12b-octahydro-indolo[2,3-a]quinolizine-1-carboxylate 7.2 g of the compound obtained in the previous stage are dissolved, under argon, in 250 cm³ of anhydrous 1,2-dimethoxyethane. After cooling the solution using an ice-bath (0° C.–5° C.), 2.4 g, of 97% sodium hydride are added in portions over a period of 15 minutes. The reaction medium is stirred at ambient temperature for 6 hours and then hydrolysed with a 4N hydrochloric acid solution at a temperature of −10° C. until a pH of 8–9 is obtained. The solvent is then distilled off in vacuo and the residue is taken up in 150 cm³ of water and 150 cm³ of ethyl acetate. Customary treatment of the organic phase yields an oil corresponding to the expected product.

Yield: 85%

Preparation B: trans-10-Methoxy-1-methoxycarbonyl-1,2,3,4,6,7,12,12b-octahydro-indol[2,3-a]quinolizinium chloride Stage A: 3-(2-Bromoethyl)-6-methoxy-indole a) Ethyl 2-(6-methoxyindol-3-yl)-2-oxoacetate 7.5 cm³ of oxalyl chloride are added dropwise, under argon and over a period of 30 minutes, to a solution of 8.3 g of 6-methoxyindole, prepared in accordance with the process described by P. L. Feldman and H. Rapoport, *Synthesis*, (1986), 736, in 100 cm³ of anhydrous diethyl ether. After stirring for two hours, the precipitate formed is separated by filtration and then suspended in 200 cm³ of ethanol.

After stirring for ten hours, the product is filtered off with suction and rinsed with diethyl ether.

Yield: 68%

Melting point: 207°–208° C.

b) 3-(2-Bromoethyl)-6-methoxy-indole 9.2 g of the compound obtained in a) are added, under argon, to 200 cm³ of anhydrous tetrahydrofuran and 4.2 g of lithium aluminium hydride. The reaction medium is heated under reflux for 3 hours. After returning to ambient temperature, the medium is hydrolysed with moist sodium sulfate. The mineral salts are removed by filtration and the filtrate is then evaporated to dryness in vacuo.

6.5 g of the residual oil obtained are dissolved again with 15 g of carbon tetrabromide in 250 cm³ of acetonitrile. The whole is cooled to from 0° C. to 5° C. and then 11.0 g of triphenylphosphine are added. After stirring for one hour, the solvent is removed by distillation in vacuo and the residue is chromatographed on a silica gel column (eluant: dichloromethane/heptane, 1:1 ) to yield the expected product.

Yield: 95%

Melting point: 109° C.

Stage B: Trans-10-methoxy-1-methoxycarbonyl-1,2,3,4,6,7,12,12b-octahydro-indolo [2.3-a]quinolizinium chloride A solution of 8.5 g of the compound obtained in stage A, 4.67 g of methyl nicotinate and 250 cm³ of acetone is heated under reflux for 48 hours. After filtering with suction and rinsing, 7.0 g of the precipitate obtained are subjected to hydrogenation with 1.5 g of 10% palladium-on-carbon in 200 cm³ of methanol in the presence of 2.9 cm³ of triethylamine. After filtering off the catalyst and concentrating in vacuo, the residue is chromatographed on a silica gel column (eluant: dichloromethane/methanol, 98:2). 4.0 g of the compound so obtained are stirred at ambient temperature for 1 hour in 20 cm³ of a solution of hydrogen chloride in methanol and 20 cm³ of diethyl ether. The precipitate is recovered, rinsed with ether and then dried.

Yield: 52%

Melting point: 250° C.

EXAMPLE 1: (2RS,7SR),(3RS,16RS)-10-Chloro-15-oxo-2,7,14,15-tetrahydro-14-aza-20,21-dinoreburnameninium chloride Stage A: Ethyl 9-chloro-1,2,3,4,6,7,7a,12,12a,12b-decahydro-indolo[2,3-a]quinolizine-1-carboxylate 5 g of sodium cyanoborohydride are added in 100 mg portions to a solution, under argon, of 6 g of the compound obtained in preparation A in 200 cm³ of trifluoroacetic acid, the reaction atmosphere being renewed with argon at each addition. The whole is stirred for 4 hours before being hydrolysed with a 10N sodium hydroxide solution, with cooling, until a pH of 9 is obtained. The reaction medium is extracted twice with 150 cm³ of diethyl ether each time. After customary treatment of the organic phase, the residual oil is heated under reflux for 1 hour in ethanol. The crude product is chromatographed on a silica gel column (eluant: methylene chloride/ethanol, 99:1 ) to yield the expected compound.

Yield: 42%

Melting point: 124° C.

Stage B: Ethyl 12-amino-9-chloro-1,2,3,4,6,7,7a,12,12a,12b-decahydro-indolo[2,3-a]quinolizine-1-carboxylate 6.0 g of the previously obtained compound are dissolved in 50 cm³ of acetic acid and 25 cm³ of water. The whole is cooled using an ice-bath and then 1.38 g of sodium nitrite in 15 cm³ of water are added. Stirring is maintained for 30 minutes at a temperature below 10° C. The reaction mixture is then rendered alkaline using a 28% ammonia solution and subsequently diluted with 200 cm³ of ethanol.

15 g of ammonium carbonate and 10 g of zinc powder are then added. The suspension is stirred vigorously for 3 hours at a temperature below 10° C. After removing the mineral salts by filtration, the filtrate is taken up in methylene chloride. After customary treatment of the organic phase, the residue is purified on a silica gel column (eluant: methylene chloride/methanol, 99:1 ) to yield the expected product.

Yield: 52%
Melting point: 172°–175° C.

Stage C: (2RS,7SR),(3RS,16RS)-10-Chloro-15-oxo-2,7,14,15-tetrahydro-14-aza-20,21-dinoreburnameninium chloride 960 mg of 97% sodium hydride are added, under argon, to 3 g of the compound obtained in stage B dissolved in 100 cm³ of anhydrous tetrahydrofuran. The whole is heated under reflux for 3 hours, cooled to ambient temperature and hydrolysed with a few drops of water. The solvent is distilled off and the residual oil is extracted with 100 cm³ of water and 2×100 cm³ of dichloromethane. Treatment of the organic phase yields a crude product which is converted into its chloride.

Yield: 68%
Melting point: 267°–268° C.

| Elemental microanalysis: $C_{16}H_{18}ClN_3O$, HCl MW: 340.26 | | | | |
|---|---|---|---|---|
| | C % | H % | N % | Cl % |
| calculated | 56.48 | 5.63 | 12.35 | 20.84 |
| found | 56.08 | 5.61 | 12.15 | 20.90 |

EXAMPLE 2: (2RS,7SR),(3RS,16RS)-10-Chloro-14-methyl-2,7,14,15-tetrahydro-14-aza-20,21-dinoreburnamenin-15-one 3 cm³ of 1.6M n-butyllithium in solution in hexane are added dropwise at −30° C. and under argon to 890 mg of the compound obtained in Example 1 dissolved in 50 cm³ of anhydrous tetrahydrofuran. After stirring for 30 minutes, 710 mg of methyl iodide in 2 cm³ of anhydrous tetrahydrofuran are added. The temperature is brought back to 25° C. over a period of 1 hour 30 minutes and stirring is then maintained for 2 hours at that temperature.

The reaction medium is hydrolysed with 80 cm³ of water and the aqueous phase is extracted with ethyl acetate. Customary treatment of the organic phase yields the expected product which is purified by recrystallisation from methanol.

Yield: 56.5%
Melting point: 209°–210° C.

| Elemental microanalysis: $C_{17}H_{20}ClN_3O$ MW: 317.82 | | | | |
|---|---|---|---|---|
| | C % | H % | N % | Cl % |
| calculated | 64.25 | 6.34 | 13.22 | 11.16 |
| found | 64.19 | 6.19 | 13.20 | 11.19 |

EXAMPLE 3: (2RS,7SR),(3RS,16RS)-14-Benzyl-10-chloro-2,7,14,15-tetrahydro-14-aza-20,21-dinoreburnamenin-15-one By proceeding as in Example 2, but replacing the methyl iodide with benzyl bromide, and after a stage of purification by chromatography on silica using, in succession, dichloromethane/methanol (95:5) and then ethyl acetate as eluant, the expected compound is obtained.

Yield: 47%
Melting point: 153°–154° C.

| Elemental microanalysis: $C_{23}H_{24}ClN_3O$ MW: 393.92 | | | | |
|---|---|---|---|---|
| | C % | H % | N % | Cl % |
| calculated | 70.13 | 6.14 | 10.67 | 9.00 |
| found | 70.02 | 5.91 | 10.35 | 9.17 |

EXAMPLE 4: (2RS,7SR),(3RS,16RS)-10-Chloro-2,7,14,15-tetrahydro-14-aza-20,21-dinoreburnameninium dichloride 850 mg of lithium aluminium hydride are added to 850 mg of the compound obtained in Example 1 in 50 cm³ of anhydrous tetrahydrofuran. The reaction medium is heated under reflux for 3 hours. 40 cm³ of water saturated with sodium chloride are then added dropwise to the reaction medium, which has been cooled to 0° C.

The mixture is extracted with ethyl acetate, and customary treatment of the organic phase yields a crude product which is converted into its dichloride, which corresponds to the expected product.

Yield: 24%
Melting point: 266°–268° C.

| Elemental microanalysis: $C_{16}H_{20}ClN_3$, 2HCl MW: 362.73 | | | |
|---|---|---|---|
| | C % | H % | N % |
| calculated | 52.98 | 6.11 | 11.58 |
| found | 52.33 | 6.18 | 11.00 |

EXAMPLE 5: (3RS,16RS)-10-Chloro-14,15-dihydro-14-aza-20,21-dinoreburnamenin-15-one 700 mg of manganese dioxide are added to 305 mg of the compound obtained in Example 1 in 25 cm³ of dichloromethane. The reaction medium is stirred for 1 hour and 30 minutes at ambient temperature and then filtered over Celite. After evaporation of the filtrate, purification and recrystallisation from methanol, the title compound is obtained.

Yield: 40%
Melting point: 252°–254° C.

| Elemental microanalysis: $C_{16}H_{16}ClN_3O$ MW: 301.78 | | | |
|---|---|---|---|
| | C % | H % | N % |
| calculated | 63.68 | 5.34 | 13.92 |
| found | 63.41 | 5.26 | 13.57 |

EXAMPLES 6 TO 14:

By proceeding in a manner analogous to that in Example 1, but replacing the ethyl 9-chloro-1,2,3,4,6,7,12,12b-oc tahydro-indolo[2,3-a]quinolizine-1-carboxylate in stage A by the appropriate starting compounds, the compounds of the following Examples are obtained:

EXAMPLE 6: (2RS,7SR),(3RS,16RS)-15-Oxo-2,7,14,15-tetrahydro-14-aza-20,21-dinoreburnameninium chloride Melting point: >250° C.

Elemental microanalysis: $C_{16}H_{19}N_3O$, HCl MW: 305.81

|  | C % | H % | N % |
|---|---|---|---|
| calculated | 62.84 | 6.59 | 13.74 |
| found | 62.79 | 6.58 | 13.64 |

EXAMPLE 7: (2RS,7SR),(3RS,16RS)-10-Bromo-15-oxo-2,7,14,15-tetrahydro-14-aza-20,21-dinoreburnameninium chloride Melting point: >275° C.

Elemental microanalysis: $C_{16}H_{18}BrN_3O$, HCl, 0.5 $CH_3OH$ MW: 400.73

|  | C % | H % | N % | Cl % |
|---|---|---|---|---|
| calculated | 49.46 | 5.28 | 10.49 | 8.85 |
| found | 49.28 | 5.13 | 10.14 | 8.39 |

EXAMPLE 8: (2RS,7SR),(3RS,16RS)-10-Methoxy-15-oxo-2,7,14,15-tetrahydro-14-aza-20,21-dinoreburnameninium chloride Melting point: 110°–112° C.

Elemental microanalysis: $C_{17}H_{21}N_3O_2$, HCl, 0.5 $CH_3OH$ MW: 351.93

|  | C % | H % | N % | Cl % |
|---|---|---|---|---|
| calculated | 59.65 | 6.82 | 11.93 | 9.93 |
| found | 59.25 | 6.88 | 11.29 | 9.62 |

EXAMPLE 9: (2RS,7SR),(3RS,16RS)-11-Methoxy-15-oxo-2,7,14,15-tetrahydro-14-aza-20,21-dinoreburnameninium chloride Melting point: >280° C.

Elemental microanalysis: $C_{17}H_{21}N_3O_2$, HCl MW: 335.84

|  | C % | H % | N % |
|---|---|---|---|
| calculated | 60.21 | 6.41 | 12.34 |
| found | 60.80 | 6.60 | 12.51 |

EXAMPLE 10: (2RS,7SR),(3RS,16RS)-10,11-Dimethoxy-15-oxo-2,7,14,15-tetrahydro-14-aza-20,21-dinoreburnameninium chloride Melting point: 282° C.

Elemental microanalysis: $C_{18}H_{23}N_3O_3$ HCl, MW: 365.90

|  | C % | H % | N % |
|---|---|---|---|
| calculated | 59.09 | 6.61 | 11.49 |
| found | 58.81 | 6.46 | 11.13 |

EXAMPLE 11: (2RS,7SR),(3RS,16RS)-10-Trifluoromethoxy-2,7,14,15-tetrahydro-14-aza-20,21-dinoreburnamenin-15-one Melting point: 74°–75° C.

Elemental microanalysis: $C_{17}H_{18}F_3N_3O_2$ MW : 353.35

|  | C % | H % | N % |
|---|---|---|---|
| calculated | 57.78 | 5.13 | 11.89 |
| found | 58.12 | 5.46 | 11.38 |

EXAMPLE 12: (2RS,7SR),(3RS,16RS)-10,11-Methylenedioxy-15-oxo-2,7,14,15-tetrahydro-14-aza-20,21-dinoreburnameninium chloride Melting point: 268°–269° C.

Elemental microanalysis: $C_{17}H_{19}N_3O_3$, HCl MW: 349.82

|  | C % | H % | N % |
|---|---|---|---|
| calculated | 58.14 | 5.82 | 11.77 |
| found | 57.99 | 6.00 | 11.48 |

EXAMPLE 13: (2RS,7SR),(3RS,16RS)-10-Methyl-15-oxo-2,7,14,15-tetrahydro-14-aza-20,21-dinoreburnameninium chloride Melting point: 280° C.

Elemental microanalyis: $C_{17}H_{21}N_3O$, HCl, 0.5 $CH_3OH$ MW: 335.84

|  | C % | H % | N % | Cl % |
|---|---|---|---|---|
| calculated | 62.58 | 7.20 | 12.51 | 10.55 |
| found | 62.47 | 7.37 | 11.85 | 10.32 |

EXAMPLE 14: (2RS,7SR),(3RS,16RS)-11-Methyl-15-oxo-2,7,14,15-tetrahydro-14-aza-20,21-dinoreburnameninium chloride Melting point: >275° C.

Elemental microanalysis: $C_{17}H_{21}N_3O$, HCl MW: 319.81

|  | C % | H % | N % | Cl % |
|---|---|---|---|---|
| calculated | 63.85 | 6.93 | 13.14 | 11.08 |
| found | 63.54 | 6.64 | 13.07 | 11.15 |

EXAMPLE 15: (2RS,7SR),(3RS,16RS)-10-Chloro-2,7,14,15-tetrahydro-14-aza-20,21-dinoreburnamenine-15-thione 305 mg of the compound obtained in Example 1 in 50 cm$^3$ of anhydrous toluene are placed in the presence of 400 mg of Lawesson's reagent. The whole is heated under toluene reflux for 1 hour 30 minutes and then hydrolysed with 50 cm$^3$ of 0.5N sodium hydroxide. Customary treatment of the organic phase yields the expected product.

Melting point: 194° C.

| Elemental microanalysis: $C_{16}H_{18}ClN_3S$ MW: 319.86 | | | | |
|---|---|---|---|---|
| | C % | H % | N % | S % |
| calculated | 60.08 | 5.67 | 13.14 | 10.02 |
| found | 59.93 | 5.78 | 13.00 | 9.98 |

EXAMPLE 16: 14,15-Dihydro-3,16-didehydro-14-aza-20,21-dinoreburnamenin-15-one 810 mg of the compound obtained in Example 6 are dissolved in a mixture composed of 10 cm$^3$ of acetic acid and 0.2 cm$^3$ of nitric acid. After stirring for 1 hour and 30 minutes at +10° C., ammonia is added until a pH of approximately 10 is obtained. The precipitate formed is isolated by filtration, washed with water and dried in vacuo before being purified by chromatography on a silica gel column (eluant: dichloromethane/methanol, 97:3). 100 mg of a yellow solid corresponding to the expected product are obtained.

Yield: 13%

Melting point: 260° C. (decomposition)

EXAMPLE 17: Trans-(3RS,16RS)-14,15-dihydro-14-aza-20,21-dinoreburnamenin-15-one 800 mg of manganese oxide are added to 250 mg of the compound of Example 6 in 25 cm$^3$ of dichloromethane. The reaction is carried out for 2 hours. The reaction medium is filtered over Celite. The filtrate is evaporated and the residue is purified by recrystallisation from ethanol to yield 170 mg of the expected compound.

Melting point: 254°–255° C.

| Elemental microanalysis: $C_{16}H_{17}N_3O$ MW: 267.33 | | | |
|---|---|---|---|
| | C % | H % | N % |
| calculated | 71.89 | 6.41 | 15.72 |
| found | 72.23 | 6.47 | 15.68 |

EXAMPLE 18: Trans-(3RS,16RS)-14,15-dihydro-14-aza-20,21-dinoreburnameninium dichloride Stage A: Trans-(3RS,16RS)-14,15-dihydro-14-aza-20,21-dinoreburnamenine 36 mg of lithium aluminium hydride are added to 170 mg of the compound obtained in Example 17 in solution in 20 cm$^3$ of tetrahydrofuran. After stirring for 2 hours, the whole is hydrolysed, the mineral salts are removed by filtration and the filtrate is evaporated to dryness.

Melting point: 196° C.

| Elemental microanalysis: $C_{16}H_{19}N_3$ MW: 253.35 | | | |
|---|---|---|---|
| | C % | H % | N % |
| calculated | 75.08 | 7.27 | 16.36 |
| found | 75.85 | 7.56 | 16.59 |

Stage B: Trans-(3RS,16RS)-14,15-dihydro-14-aza-20,21-dinoreburnameninium dichloride The compound obtained in the previous stage is convened into its dichloride in a solution of hydrogen chloride in ethanol to yield 100 mg of the expected compound.

Global yield: 57%

Melting point: 239°–240° C.

| Elemental microanalysis: $C_{16}H_{19}N_3$, 2HCl MW: 326.27 | | | | |
|---|---|---|---|---|
| | C % | H % | N % | Cl % |
| calculated | 58.90 | 6.49 | 12.88 | 21.73 |
| found | 59.06 | 6.22 | 12.84 | 21.88 |

EXAMPLE 19: (2SR,7RS),(3RS,16RS)-2,7,14,15-Tetrahydro-14-aza-20,21-dinoreburnameninium dichloride The procedure is identical with that described in Example 18, starting from the compound obtained in Example 6.

Yield: 78%

Melting point: >275° C.

| Elemental microanalysis: $C_{16}H_{21}N_3$, 2HCl MW: 328.29 | | | | |
|---|---|---|---|---|
| | C % | H % | N % | Cl % |
| calculated | 58.54 | 7.06 | 12.80 | 21.60 |
| found | 58.82 | 7.43 | 12.50 | 20.81 |

EXAMPLE 20: (1aRS,12bRS),(7aSR,12aRS)-9-Chloro-1a,2,3,6,7,7a,12a,12b-octahydro-1H,4H-benzo[5,6]pyrrolizino[2,1,7-ija]quinolizin-1-one 80 mg of 97% sodium hydride are added, under argon, to 250 mg of the compound obtained in stage A of Example 1 in 25 cm$^3$ of anhydrous tetrahydrofuran. The whole is heated under reflux for 3 hours, then cooled to ambient temperature and hydrolysed with a few drops of water. The solvent is evaporated and the residue is taken up in 20 cm$^3$ of water and 2×15 cm$^3$ of dichloromethane. Customary treatment of the organic phase yields a crude product which, after recrystallisation from diisopropyl ether, corresponds to the expected product.

Yield: 85%

Melting point: 176°–177° C.

| Elemental microanalysis: $C_{16}H_{17}ClN_2O$ MW: 288.78 | | | | |
|---|---|---|---|---|
| | C % | H % | N % | Cl % |
| calculated | 66.55 | 5.93 | 9.70 | 12.28 |
| found | 66.62 | 5.61 | 9.30 | 12.24 |

EXAMPLE 21: (1aRS,12bRS),(7aSR,12aRS)-9-Methyl-1a,2,3,6,7,7a,12a,12b-octahydro-1H,4H-benzo[5,6]pyrrolizino[2,1,7-ija]quinolizin-1-one By proceeding in the manner indicated in the previous Example and starting from the compound obtained in the first stage of Example 13, the expected product is obtained.

Yield: 78%

Melting point: 152°–153° C.

| Elemental microanalysis: $C_{17}H_{20}N_2O$ MW: 268.36 | | | |
|---|---|---|---|
| | C % | H % | N % |
| calculated | 76.09 | 7.51 | 10.44 |
| found | 76.28 | 7.55 | 10.40 |

EXAMPLE 22: (1aRS,12bRS),(7aSR,12aRS)-9-Methoxy-1a2,3,6,7,7a,12a,12b-octahydro-1H,5H-benzo[5,6]pyrrolizino[2,1,7-ija]quinolizin-1-one By proceeding as described in Example 20 and starting from the compound obtained in the first stage of Example 8, the expected product is obtained.

Yield: 86%

Melting point: 145°–146° C.

| Elemental microanalysis: $C_{17}H_{20}N_2O2$ MW: 284.36 | | | |
|---|---|---|---|
| | C % | H % | N % |
| calculated | 71.81 | 7.09 | 9.85 |
| found | 71.63 | 7.02 | 9.90 |

EXAMPLE 23: (2RS,7SR),(3RS,16RS)-14-Benzyl-2,7,14,15-tetrahydro-14-aza-20,21-dinoreburnamenin-15-one 1.2 cm³ of 1.6M n-butyllithium in hexane are added under argon and at −30° C. to 270 mg of the compound obtained in Example 6 in 10 cm³ of anhydrous tetrahydrofuran. After stirring for 30 minutes, 250 mg of benzyl bromide are added. After returning to ambient temperature (2 hours), the reaction medium is stirred for 16 hours, then hydrolysed and extracted with ethyl acetate. Customary treatment of the organic phase yields a product which is purified by chromatography on a silica gel column (eluant: ethyl acetate) to yield 250 mg of the expected compound.

Yield: 71%

Melting point: 122° C.

| Elemental microanalysis: $C_{23}H_{25}N_3O$ MW: 359.48 | | | |
|---|---|---|---|
| | C % | H % | N % |
| calculated | 75.85 | 7.01 | 11.69 |
| found | 75.26 | 6.88 | 11.05 |

EXAMPLE 24: Trans-(3RS,16RS)-14-benzyl-14,15-dihydro-14-aza-20,21-dinoreburnamenin-15-one 50 mg of 97% sodium hydride are added under argon to 100 mg of the compound obtained in Example 17 in 15 cm³ of anhydrous tetrahydrofuran heated to 50° C. After 20 minutes' reaction, 170 mg of benzyl bromide in 2 cm³ of tetrahydrofuran are added dropwise. After two hours, the reaction medium is cooled, the excess hydride is destroyed with water and the reaction mixture is extracted with ethyl acetate. Treatment of the organic phase yields a crude product which is recrystallised from methanol to yield, after drying, 100 mg of the expected compound.

Yield: 75%

Melting point: 158° C.

| Elemental microanalysis: $C_{23}H_{23}N_3O$ MW: 357.46 | | | |
|---|---|---|---|
| | C % | H % | N % |
| calculated | 77.28 | 6.49 | 11.76 |
| found | 76.93 | 6.35 | 11.80 |

PHARMACOLOGICAL STUDY

EXAMPLE A: Study of the tyrosine hydroxylase-inducing effect

The animals used are male Sprague-Dawley rats (Iffa-Credo, France) weighing 220–250 g which are placed in a chamber at a temperature of 22° C. with a light/darkness cycle of 12 h/12 h. Food is provided as desired, as is water. The animals are treated with a single dose (intraperitoneal mode) of the product, the controls receiving the carrier solution. In order to study the inducing effect, the animals are sacrificed 3 days after the injection.

After the animals have been sacrificed by decapitation, the brain is removed rapidly and then frozen on a metal plate cooled to −80° C. The structures are dissected in serial 200 mm sections. The frozen brains are cut along the posterior-anterior axis using a refrigerated microtome having a plate. The tissues are removed using a punch thanks to a metal tube having an inside diameter of 2 mm. Under those conditions, the structures are removed in excess. Eight sections of 200 mm (4 for the locus posterior, 4 for the locus anterior) and eight sections of 200 mm (for the substantia nigra) are obtained along the posterior-anterior axis. In order to improve the reproducibility of the removal procedures, the latter were carried out after histochemical visualisation of the structures by Glenner's colorimetric method (1957). The principle of that technique is based on the oxidation of a substrate. tryptamine, supplied to the incubated sections, by endogenous monoamine oxidase (MAO) which is involved in the degradation of catecholamines. The product oxidised by MAO then reduces tetrazolium salts in the incubation bath, which precipitate.

The brain structures are placed in a phosphate buffer (5 mM, pH 6) containing 0.2% of Triton X-100, which enables the proteins, especially the membrane TH, to be completely solubilised. The extraction of the TH is effected with 3 freezing/thawing cycles (−80° C./ambient temperature) followed by centrifugation at 10,000 g for 20 minutes at +4° C. The amount of TH is measured by immunoautoradiography (dot blot method). Briefly, the protein is deposited directly on a sheet of nitrocellulose saturated with a 1% bovine serum albumin solution (BSA) for ½ h and incubated overnight in a monoclonal anti-TH antibody solution diluted to 1/3000. Any complex is revealed alter 2 hours' incubation in a solution of radioactive ($^{135}$I) protein A diluted to 1/1000. After exposing the nitrocellulose on an MP film for approximately from 4 to 7 days, the film is developed under standard conditions. The signal obtained for each deposit is quantified by densitometry using an Imstar image analyser. The amount of TH (expressed in TH units per structure) is calculated from a standard suprarenal TH scale. The results are set out in the following Table I:

TABLE I

Measurement of the amount of TH in the anterior locus coeruleus (ALC) and the posterior locus coeruleus (PLC) after ip. administration (30 mg/kg)

| Ex. No. | ALC | PLC |
|---------|-----|-----|
| 1 | +45%*** | +30%*** |
| 8 | +45%*** | +30%*** |
| 9 | +49%** | +19% (ns)[(1)] |
| 13 | +15%** | +15%** |
| 14 | +44%** | +22% (ns) |
| 18 | +47%** | +28%* |
| 20 | +20% | 0% |
| 21 | +30%* | 0% |
| 22 | +40%* | 0% |

[(1)]+14%* in the substantia nigra
ns: non-specific
*p <0.05
**p <0.01
***p <0.001

We claim:

1. A compound selected from those of formula (I):

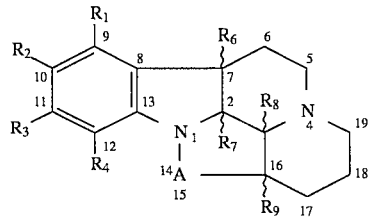

wherein:

$R_1$, $R_2$, $R_3$ and $R_4$, which may be identical or different, are:

selected independently of one another from:

hydrogen, halogen, hydroxy, linear or branched ($C_1$–$C_6$)-alkyl optionally substituted by halogen, by one or more amino, by one or more nitro, by linear or branched ($C_1$–$C_6$)-alkoxy and/or by aryl, selected from phenyl and naphthyl, which are themselves optionally substituted by halogen, nitro, amino, ($C_1$–$C_6$)-alkyl and/or ($C_1$–$C_6$)-alkoxy, and linear or branched ($C_1$–$C_6$)-alkoxy optionally substituted by halogen, by amino, by one or more nitro, and/or by one or more linear or branched ($C_1$–$C_6$)-alkoxy, or $R_1$, $R_2$, $R_3$ and $R_4$, taken in pairs and carded by adjacent carbon atoms, form methylenedioxy or ethylenedioxy, $R_6$ and $R_7$: either each simultaneously represents hydrogen, adopting a cis-configuration with respect to one another, or together form a bond, no two adjacent $R_1$ through $R_4$ groups being tertiary butyl, $R_8$ and $R_9$: either each simultaneously represents hydrogen, adopting a cis- or trans-configuration with respect to one another, or together form a bond, in which case $R_6$ and $R_7$ also together form a bond, A represents the bivalent radical
wherein
Z is selected from oxygen and sulfur, $R_5$ is selected from hydrogen and linear or branched ($C_1$–$C_6$)-alkyl optionally its optical isomers alone or in admixture, and where appropriate, their pharmaceutically-acceptable addition salts with an acid.

2. A compound according to claim 1 which is selected from 9-methoxy-1a,2,3,6,7,7a,12a,12b-octahydro-1H,5H-benzo[5,6]pyrrolizino[2,1,7-ija]quinolizin-1-one, its optical isomers, alone or in mixture, or its pharmaceutically-acceptable addition salts with an acid.

3. A method for treating a condition of depression or anxiety in a mammal comprising the step of administering to said mammal an amount of a compound of claim 1 which is effective for alleviation of said condition.

4. A pharmaceutical composition useful in treating depression or anxiety which contains as active ingredient an effective amount of an inducer of a tyrosine hydroxylase compound of claim 1, in combination with a pharmaceutically-acceptable excipient or vehicle.

* * * * *

UNITED STATES PATENT AND TRADEMARK OFFICE
CERTIFICATE OF CORRECTION

PATENT NO. : 5,622,957
DATED : April 22, 1997                                       Page 1 of 2
INVENTOR(S) : J.D. Brion; C. Thal; L. Demuynck;
J.G. Parmentier; J. Lepagnol; P. Lestage;
J.F. Pujol; P. Schmitt; P. Potier It is certified that error appears in the above-indentified patent and that said Letters Patent is hereby corrected as shown below:

Column 1, line 59: Insert -- * -- at beginning of the line. Page 2, line 4

Column 5, lines 63 & 64: "(I1), (I2) and (I3)," should read -- (I/1), (I/2) and (I/3), --. Page 6, line 19; and Page 7, lines 5 & 9

Column 7, line 56: "-indol[2,3-a]" should read -- -indolo[2,3-a] --. Page 10, line 13

Column 17, line 44: Delete "one or more" in both instances. See page 3 of Response and Amendment dtd 7/16/96, Claim 1, page 23, line 11.

Column 18, lines 5 and 6: Delete "one or more" in both instances. See page 3 of Response and Amendment dtd 7/16/96, Claim 1, page 23, line 16.

Column 18, line 7: After "alkoxy," insert -- no two adjacent $R_1$ through $R_4$ groups being tertiary butyl, --. See page 3 of Response and Amendment dtd 7/16/96, Claim 1, page 23, line 17.

Column 18, line 9: "carded" should read -- carried --. Page 23, line 18

UNITED STATES PATENT AND TRADEMARK OFFICE
CERTIFICATE OF CORRECTION

PATENT NO. : 5,622,957
DATED : April 22, 1997
INVENTOR(S) : J.D. Brion; C. Thal; L. Demuynck;
J.G. Parmentier; J. Lepagnol; P. Lestage;
J.F. Pujol; P. Schmitt; P. Potier It is certified that error appears in the above-indentified patent and that said Letters Patent is hereby corrected as shown below:

Column 18, line 16 : Delete the line starting with "no two" and ending with "butyl". Page 23, line 23

Column 18, lines 26 and 27: Delete "$R_5$ is selected from hydrogen and linear or branched ($C_1$-$C_6$) alkyl optionally". Page 2 of Preliminary Amendment dtd 4/28/95, Claim 1 on page 24, lines 5 through 16.

Signed and Sealed this

Twelfth Day of August, 1997

Attest:

BRUCE LEHMAN

Attesting Officer

Commissioner of Patents and Trademarks